(12) United States Patent
Wickham et al.

(10) Patent No.: US 6,269,839 B1
(45) Date of Patent: Aug. 7, 2001

(54) CONTROL MEMBER FOR A VALVE AND METHOD FOR DETERMINING FLUID FLOW RATE THROUGH A VALVE

(75) Inventors: Peter John Deacon Wickham, Five Dock; Ian Malcolm Smith, Westleigh; Denis Bullock, Ryde; Patrick John McAuliffe, Carlingford, all of (AU)

(73) Assignee: ResMed (R&D) Limited (AU)

( * ) Notice: Subject to any disclaimer, the term of this patent is extended or adjusted under 35 U.S.C. 154(b) by 0 days.

(21) Appl. No.: 09/370,920

(22) Filed: Aug. 9, 1999

(30) Foreign Application Priority Data

Aug. 7, 1998 (AU) ................................................ PP5123

(51) Int. Cl.[7] ................................................ F16K 11/052
(52) U.S. Cl. .................... 137/625.65; 137/625.2
(58) Field of Search ............................. 137/625.2, 625.65

(56) References Cited

U.S. PATENT DOCUMENTS

| | | |
|---|---|---|
| 4,277,832 | 7/1981 | Wong . |
| 4,938,252 | 7/1990 | Piechnick . |
| 4,976,237 | 12/1990 | Bollinger . |
| 5,349,983 | 9/1994 | Ozarowski et al. . |
| 5,474,062 | 12/1995 | DeVires et al. . |
| 5,522,416 | 6/1996 | Farrell et al. . |
| 5,598,838 | 2/1997 | Servidio et al. . |
| 5,878,765 | 3/1999 | Lange . |
| 5,931,163 | 8/1999 | Stegmann et al. . |

FOREIGN PATENT DOCUMENTS 0 086 259   8/1983  (EP) .

*Primary Examiner*—Gerald A. Michalsky
(74) *Attorney, Agent, or Firm*—Pillsbury Winthrop LLP

(57) ABSTRACT

A control member is rotatable to alter a control flow area of a primary flow path of a valve, with the control flow area being of a rectangular shape having a side defined by a wall of a valve interior, a side defined by a wall of a control member exterior, a bottom defined by a floor of the valve interior and a top defined by a roof of the valve interior. The control member exterior is so configured that rotation of the control member alters a distance between the control member exterior and the wall of the valve interior to alter the control flow area of the primary flow path, with the amount of rotation of the control member between two predetermined end positions and the alteration in the control flow area of the primary flow path being substantially linearly proportional.

10 Claims, 6 Drawing Sheets

CONTROL MEMBER FOR A VALVE AND METHOD FOR DETERMINING FLUID FLOW RATE THROUGH A VALVE

FIELD OF THE INVENTION

The present invention relates to a control member for a valve and method for determining fluid flow rate through a valve.

The invention has been developed primarily for a flow diverting valve used in controlling the pressure and flow rate, and measuring the flow rate, of a breathable gas supplied to the airways of a patient by a breathable gas supply apparatus during, for example, nasal Continuous Positive Airway Pressure (CPAP) treatment of Obstructive Sleep Apnea (OSA) and ventilatory assistance treatments such as non-invasive positive pressure ventilation (NIPPV). However, it will be appreciated that the invention is not limited to these particular uses and is equally applicable to controlling and measuring the flow of any fluid (ie. gas or liquid) passing a control member of a valve.

BACKGROUND OF THE INVENTION

CPAP treatment is a common ameliorative treatment for breathing disorders including OSA. CPAP treatment, as described in U.S. Pat. No. 4,944,310, provides pressurised air or other breathable gas to the entrance of a patient's airways at a pressure elevated above atmospheric pressure, typically in the range 3–20 cm $H_2O$.

It is known for the level of treatment pressure to vary during a period of treatment accordance with patient need, that form of CPAP being known as automatically adjusting nasal CPAP treatment, as described in U.S. Pat. No. 5,245,995.

NIPPV is another form of treatment for breathing disorders which can involve a relatively higher pressure of gas being provided in the patient mask during the inspiratory phase of respiration and a relatively lower pressure or atmospheric pressure being provided in the patient mask during the expiratory phase of respiration.

In other NIPPV modes the pressure can be made to vary in a complex manner throughout the respiratory cycle. For example, the pressure at the mask during inspiration or expiration can be varied through the period of treatment, as disclosed in the applicant's international PCT patent application No. PCT/AU97/00631.

Typically, the ventilatory assistance for CPAP or NIPPV treatment is delivered to the patient by way of a nasal mask. Alternatively, a mouth mask or full face mask or nasal prongs can be used. In this specification any reference to a mask is to be understood as incorporating a reference to a nasal mask, mouth mask, full face mask or nasal prongs, unless otherwise specifically indicated.

In this specification any reference to CPAP treatment is to be understood as embracing all of the above described forms of ventilatory treatment or assistance.

Breathable gas supply apparatus broadly comprise a flow generator constituted by a continuous source of air or other breathable gas generally in the form of a blower driven by an electric motor. The electric motor driving the blower is typically controlled by a servo-controller under the control of a microcontroller unit. A hospital piped supply can also be used. The gas supply is connected to a conduit or tube, which is in turn connected to a patient mask which incorporates, or has in close proximity, a vent to atmosphere for exhausting exhaled gases.

International PCT patent application No. PCT/AU96/00586 (International Publication No. WO 97/10868) discloses a flow diverting valve with a rotatable control member, see FIGS. 19a and 19b of that application. The valve also has an inlet in fluid communication with a flow generator, an outlet in fluid communication with the patient's airways and a vent in fluid communication with atmosphere. The rotatable control member disclosed can be positioned to close the vent and open a flow path from the valve inlet to the valve outlet for supplying gas during patient inhalation, and throttle or restrict the inlet and open a flow path from the patient to the vent to change the pressure or flow delivered by the circuit to the patient. The valve is thus suitable for use in a CPAP or NIPPV gas supply circuit.

It is an object of the present invention to provide an improved flow control member for a valve and, in a preferred form, a flow control member that allows simplification of an associated closed loop feedback control system and flow rate determination method.

SUMMARY OF THE INVENTION

Accordingly, in a first aspect, the present invention provides a control member for a valve, the valve having an inlet, an outlet and a primary flow path therebetween, the control member being rotatable to alter a control flow area of the primary flow path, wherein the amount of rotation of the control member between two predetermined end positions causes a substantially linearly proportional alteration in the control flow area of the primary flow path.

Preferably, at all rotational positions of the control member, the control area is the minimum cross-sectional area between the valve interior and the control member exterior downstream of the inlet.

The control flow area can be of any shape. In a preferred embodiment, the control flow area is a rectangular shape having a side defined by a wall of the valve interior, a side defined by a wall of the control member exterior, a bottom defined by the floor of the valve interior and a top defined by the roof of the valve interior.

The interior of the control member is preferably controlled by a stepper motor, servo motor or other rotary actuator.

The two predetermined end positions preferably correspond to the control flow area being at a maximum and a minimum respectively. The minimum control flow area is preferably the primary flow path being substantially occluded or closed.

In a preferred form, the valve also includes a vent to atmosphere and a secondary flow path between the valve outlet and the vent, wherein the rotation of the control member is also adapted to alter a control flow area of the secondary flow path.

The control flow area of the secondary flow path is preferably the minimum cross-sectional area between the housing interior and the control member exterior upstream of the vent.

The control member is preferably adapted such that increasing the control area of the primary flow path simultaneously decreases the control area of the secondary flow path and vice versa.

Preferably, when the control flow area of the primary flow path is maximised or fully opened the control flow area of the secondary flow path is minimised or fully closed, and when the control flow area of the primary flow path is minimised or fully closed the control flow area of the secondary path is at least partially opened and more preferably fully opened.

In a second aspect, the present invention provides a method of determining fluid flow rate through a valve, the valve having an inlet, an outlet, a primary flow path between the inlet and outlet and a control member adapted to be moved to alter a control flow area of the primary flow path, wherein the amount of movement of the control member between two predetermined end positions causes a substantially linearly proportional alteration of the control flow area of the primary flow path, said method including the steps of:

sensing the fluid pressure at the inlet and outlet;

sensing the position of the control member; and determining the fluid flow rate from a predetermined function of fluid flow rate relative to the sensed fluid pressures and the sensed control member position.

Preferably, the control member is moved by being rotated.

The control member is preferably rotated by a stepper motor, servo motor or other rotary actuator.

In an embodiment, the valve also has a vent to atmosphere and a secondary flow path between the outlet and the vent. In this embodiment, the method includes the step of sensing the fluid pressure at the inlet, the outlet and the vent. In a variation of this embodiment, the vent is preferably substantially unrestricted and only the pressure at the inlet and the outlet is sensed because the pressure at the vent can be assumed to be at or close to atmospheric pressure.

In one embodiment, the predetermined function represents measurement of fluid flow rate at the outlet at predetermined control member positions over a range of inlet, outlet and/or vent pressures. In an alternative embodiment, the function represents measurements of fluid flow rate at the outlet at predetermined inlet, outlet and/or vent pressures over a range of control member positions.

Once the outlet flow rate is known with respect to the inlet and outlet and/or vent pressures and control member position a preferred form of the method allows for the outlet flow to the patient to be determined by reference to the predetermined function. This advantageously allows determination of patient instantaneous flow without the need to provide for a separate flow meter to measure same. In a CPAP or NIPPV application, determination of patient instantaneous flow is often required to allow for the monitoring and use of related patient flow parameters such as tidal volume, minute ventilation, the phase of the respiratory cycle and patient airway flow limitation. This information may be established by reference to the patient instantaneous flow determined by reference to the pressure readings and control member position taken from the valve and the valve's predetermined function.

The substantially linear relationship between the flow rate and pressure drop through the control area of the valve relative to the control member position advantageously facilitates the rapid and accurate feedback control of the valve and thereby allows for the valve to provide suitable pressure and flow transitions over a very short time interval, as is beneficial in NIPPV.

DETAILED DESCRIPTION OF THE PREFERRED EMBODIMENT

Figure 1:
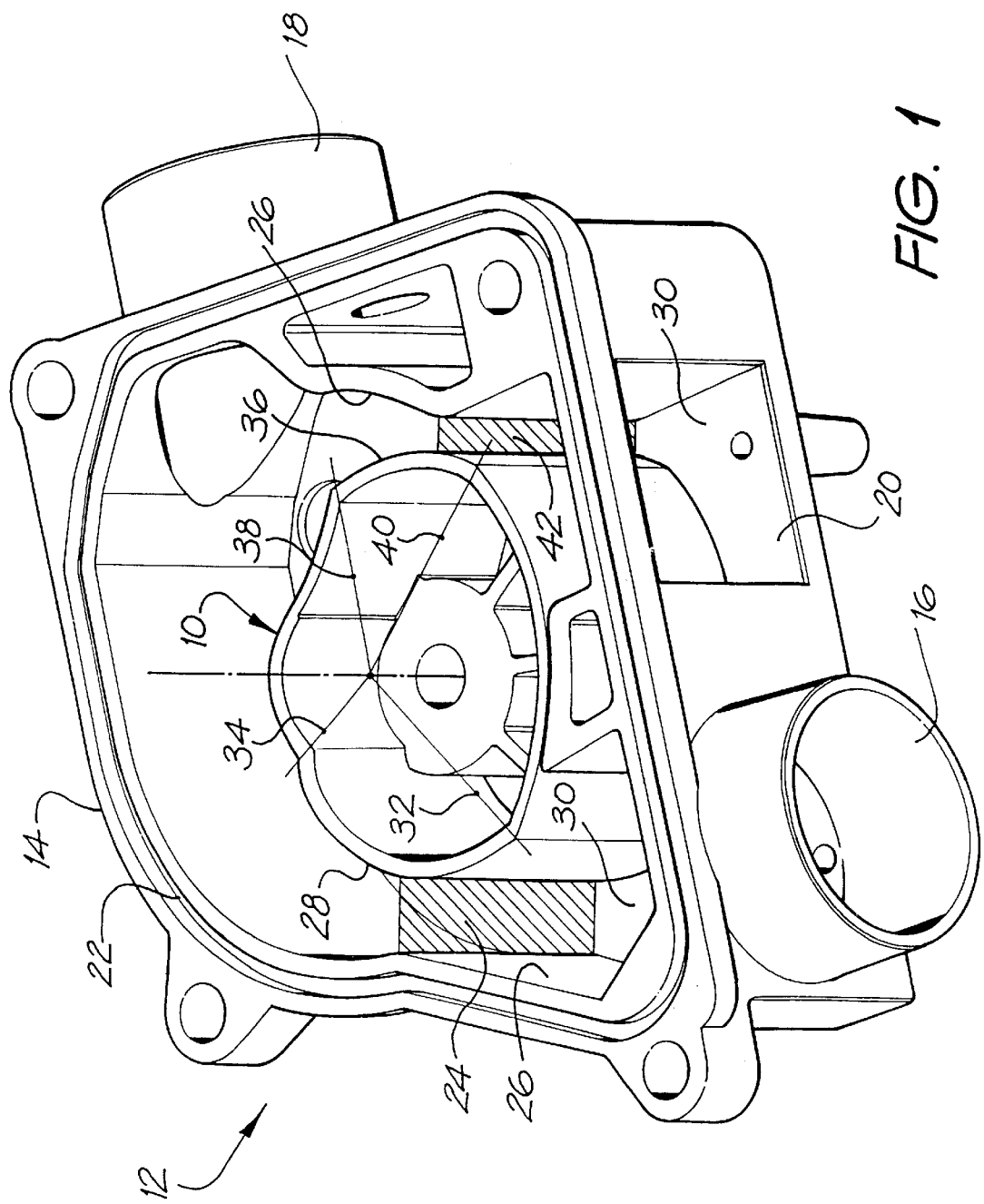
FIG. 1 is a perspective view of a valve having a first embodiment of a flow control member according to the invention with the cover removed.

FIGS. 1 to 4 show a first embodiment of a control member 10 for a valve 12. The valve 12 includes a housing 14 having an inlet duct 16 in fluid communication with the interior of the housing 14 and an outlet duct 18 in fluid communication with the interior of the housing 14. The housing 14 also includes a vent 20 opening to atmosphere also in fluid communication with the interior of the housing 14. When used for CPAP or NIPPV, the inlet duct 16 is connected to a breathable gas source such as a flow generator and the outlet duct 18 is connected to a conduct or tube connected to a patient mask.

The upper edge of the housing 14 also includes a channel 22 for locating a sealing member (not shown) against a sealing upper lid (not shown).

The minimum cross-sectional area of the flow path between the inlet duct 16 and the outlet duct 18 is indicated by rectangular hatched portion 24. The left hand side of the portion 24 is defined by interior wall 26 of the housing 14, the right hand side of the portion 24 is defined by exterior wall region 28 of the control member 10, the bottom of the portion 24 is defined by the floor 30 of the housing 14 and the top of the portion 24 is defined by the underside of the lid (not shown) of the housing 14.

The hatched portion 24 represents a control flow area of the (primary) flow path between the inlet duct 16 and the outlet duct 18 as it is the minimum cross-sectional area through which the supplied gas must flow to be communicated from the inlet duct 16 to the outlet duct 18.

The shape of the wall region 28 of the control member 10 between the regions indicated by lines 32 and 34 is configured to provide a substantially linearly proportional amount of change in the cross-sectional area of the control flow area (indicated by the hatched portion 24) in response to rotational movement of the flow control member 10 between two end positions indicated by lines 32 and 34.

Set out below is a table of the effective radius of the control member 10 between the line 32 (angle 0°) and the line 34 (angle 90°). This results in a similarly linear relationship between the gap or width of the control flow area (the hatched portion 24) relative to angular movement of the control member 10 between the two end positions 32 and 34.

| Angle of control member (degrees) | Effective radius of control member (mm) | Width of control flow area (mm) |
| --- | --- | --- |
| 0 | 20.00 | 0.00 |
| 5 | 19.28 | 0.72 |
| 10 | 18.56 | 1.44 |

-continued

| Angle of control member (degrees) | Effective radius of control member (mm) | Width of control flow area (mm) |
|---|---|---|
| 15 | 17.83 | 2.17 |
| 20 | 17.11 | 2.89 |
| 30 | 15.67 | 4.33 |
| 40 | 14.22 | 5.78 |
| 50 | 12.78 | 7.22 |
| 60 | 11.33 | 8.67 |
| 70 | 9.89 | 10.11 |
| 80 | 8.44 | 11.56 |
| 90 | 7.00 | 13.00 |

Figure 5:
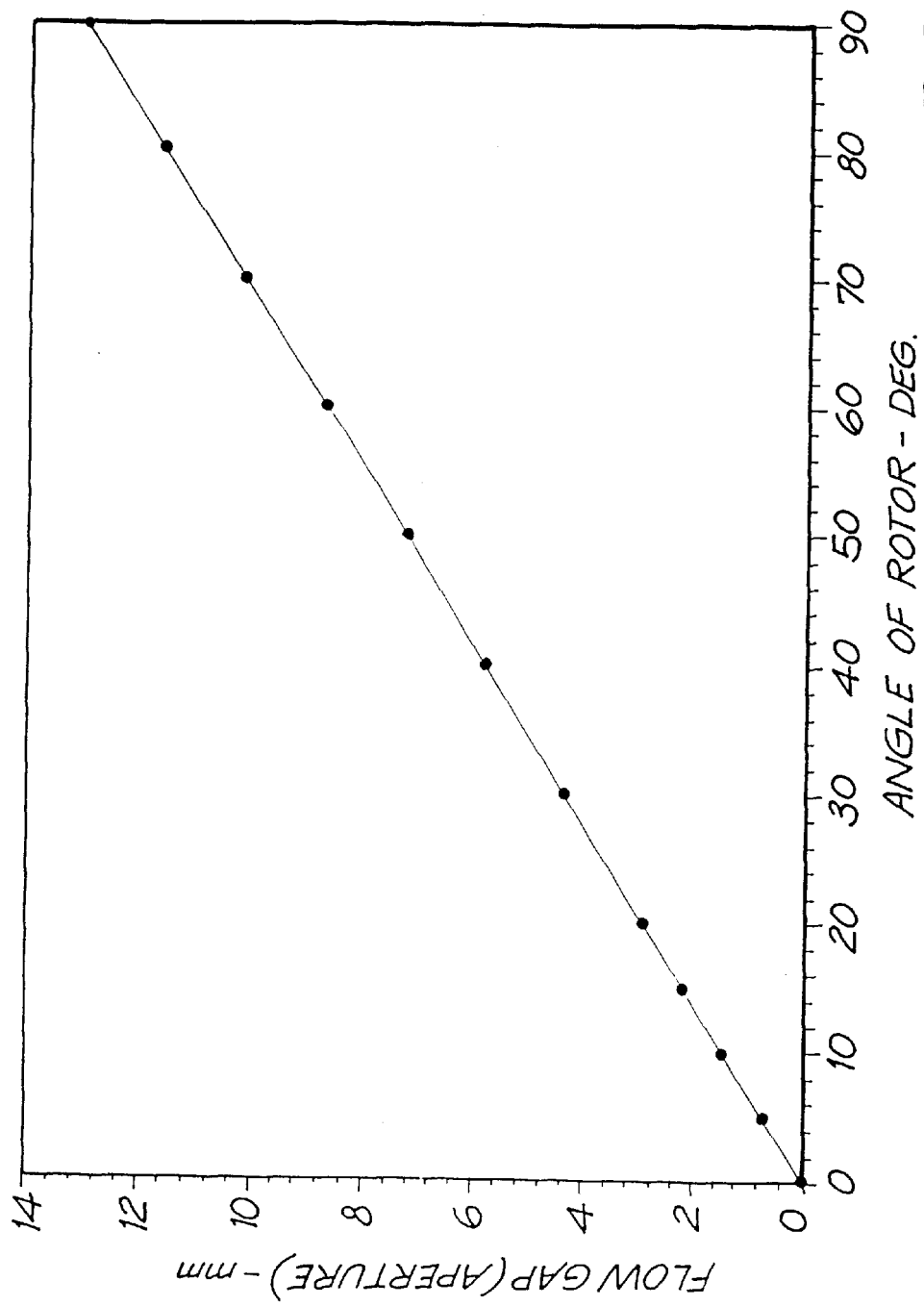
FIG. 5 is a plot of the gap between the flow control member wall and adjacent valve housing wall over a range of control member angles.

A plot of the above relationship is given in FIG. 5.

As a result of this latter substantially linear relationship, the amount of rotation of the control member 10 through the angle between the end positions 32 and 34 causes a substantially linearly proportional alteration in the area of the control flow area of the (primary) flow path between the inlet duct 16 and the outlet duct 18.

With the typical velocities and pressures of air used for CPAP and NIPPV the dominant force is friction which is proportional to gas velocity, so the pressure drop across the control flow area 24 between the inlet duct 16 and the outlet duct 18 is proportional to the velocity of the gas through the control flow area 24, and thus similarly proportional to the flow rate of the gas through the control flow area 24. Accordingly, by providing a substantially linear relationship between the position of the valve member 10 and the control flow area 24, a substantially linear relationship is provided between the position of the control member 10 and both pressure drop and flow rate.

These substantially linear relationships are extremely advantageous in closed loop feedback control of the pressure and flow rate of, for example, a breathable gas leaving the valve 12 during CPAP or NIPPV. Such control systems can be used to deliver gas to the patient mask that is at a substantially constant pressure or a changing pressure as required by a NIPPV treatment mode irrespective of breathing volume.

In particular, for a given constant inlet pressure, the pressure/flow rate is substantially linear with respect to the angular position of the control member 10. The closed loop feedback control system can thus be simplified and will be more accurate due to the avoidance of non-linear relationships. The rotation of the control member 10 is conveniently controlled by a stepper motor (not shown) incorporating a sensor indicative of the stepper motor angular position. Controlling the valve with a simplified and accurate linear closed loop feedback system enables a CPAP or NIPPV apparatus and breathing circuit to deliver the requisite pressure and flow transitions in a very small time frame, as is beneficial in NIPPV.

In accordance with an embodiment of the method of the invention a function of fluid flow rates relative to inlet and outlet and vent fluid pressure and control member position can be determined. For example, the fluid flow rate can be measured at predetermined control member positions over a range of inlet, outlet and vent pressures. Alternatively, the fluid flow rate can be measured at predetermined inlet, outlet and vent pressures over a range of control member positions. This function or data can be conveniently incorporated into a database or look up table or the like or a series of mathematical relationships which for part of the overall feedback control system for the valve 12 and associated CPAP or NIPPV apparatus.

In this way, a preferred form of the invention provides a method of determining fluid flow rate through the valve 12 by sensing the fluid pressure at or adjacent the valve inlet duct 16, the outlet duct 18 and the vent 20 and the position of the control member 10, by virtue of sensing the stepper motor position, and determining the flow rate leaving the valve 12 from the predetermined function. This method has the advantage that the overall CPAP or NIPPV apparatus can be simplified as no separate flow rate measuring mechanism such as an orifice plate or the like is required. This reduces the cost of the CPAP or NIPPV apparatus and also avoids additional air flow restriction that could be caused by the flow rate sensing mechanism.

The embodiment of the valve 12 shown in FIGS. 1 to 4 has been specifically configured for use as a flow diverting valve suitable for NIPPV which, as previously mentioned, involves supplying a relatively higher pressure of gas to the patient mask during inhalation and a relatively lower pressure or atmospheric pressure to the patient mask during exhalation or varying pressure supplied to the patient mask throughout the respiratory cycle.

In this connection, the valve member 10 also includes a wall region 36 between end positions indicated by lines 38 and 40 which, in conjunction with the valve body interior wall 26, floor 30 and lid, define a control flow area, indicated by hatched portion 42, of the (secondary) flow path between the inlet duct 18 and the vent 20. The secondary flow path allow venting of gas to atmosphere from the patient through the outlet duct 18 to the vent 20 during patient exhalation.

The wall regions 28 and 36 of the control member 10 are configured such that increasing the control flow area 24 results in simultaneous decreasing of the control flow area 42 and vice versa.

Figure 2:
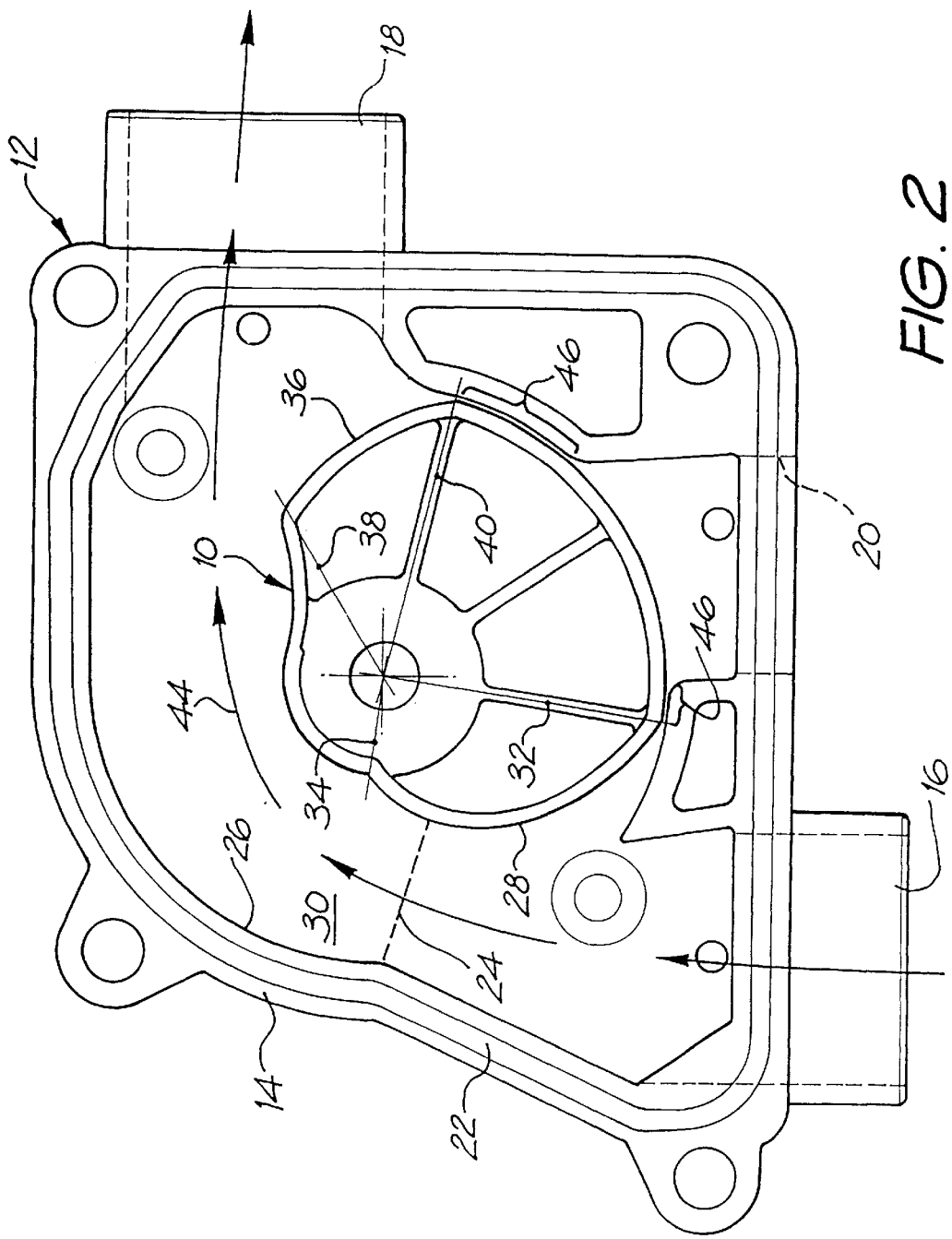
FIG. 2 is a top view of the valve shown in FIG. 1 with the inlet fully opened and the vent fully closed.

FIG. 2 shows the control member 10 placed in a position suitable for patient inhalation where the control flow area 24 adjacent the inlet 16 is maximised in order to minimise the pressure drop of the gas flow flowing from the inlet 16 to the outlet 18. This maximises the flow rate of the gas supplied to the patient for inhalation, as indicated by arrows 44. In this position the control flow area 42 between the outlet duct 18 and vent 20 is substantially closed.

The overlap between the control member exterior wall and housing interior wall in regions 46 improves sealing between the control member 10 at the interior of the housing 14.

Figure 3:
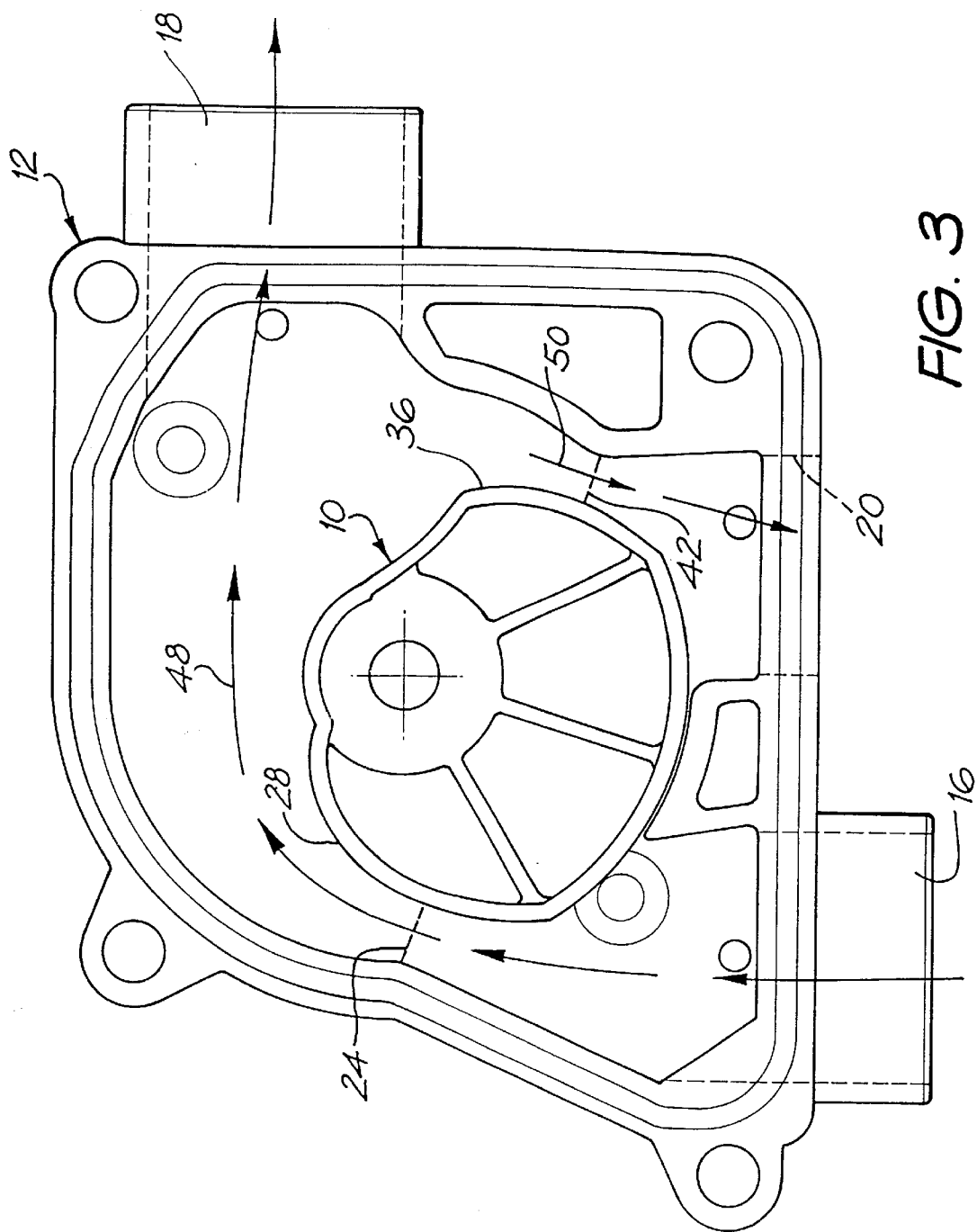
FIG. 3 is a top view of the valve shown in FIG. 1 with the inlet partially opened and the vent partially opened.

FIG. 3 shows the control member 10 placed in another position suitable for patient inhalation in which the gas flowing from the inlet 16 to the outlet 18, indicated by arrows 48, is partially throttled by a reduction in the control flow area 24. In this position, the control flow area 42 adjacent the vent 20 is partially opened allowing some residual flow therethrough, as indicated by arrows 50, for supplying a less than maximum flow of gas to the patient.

Figure 4:
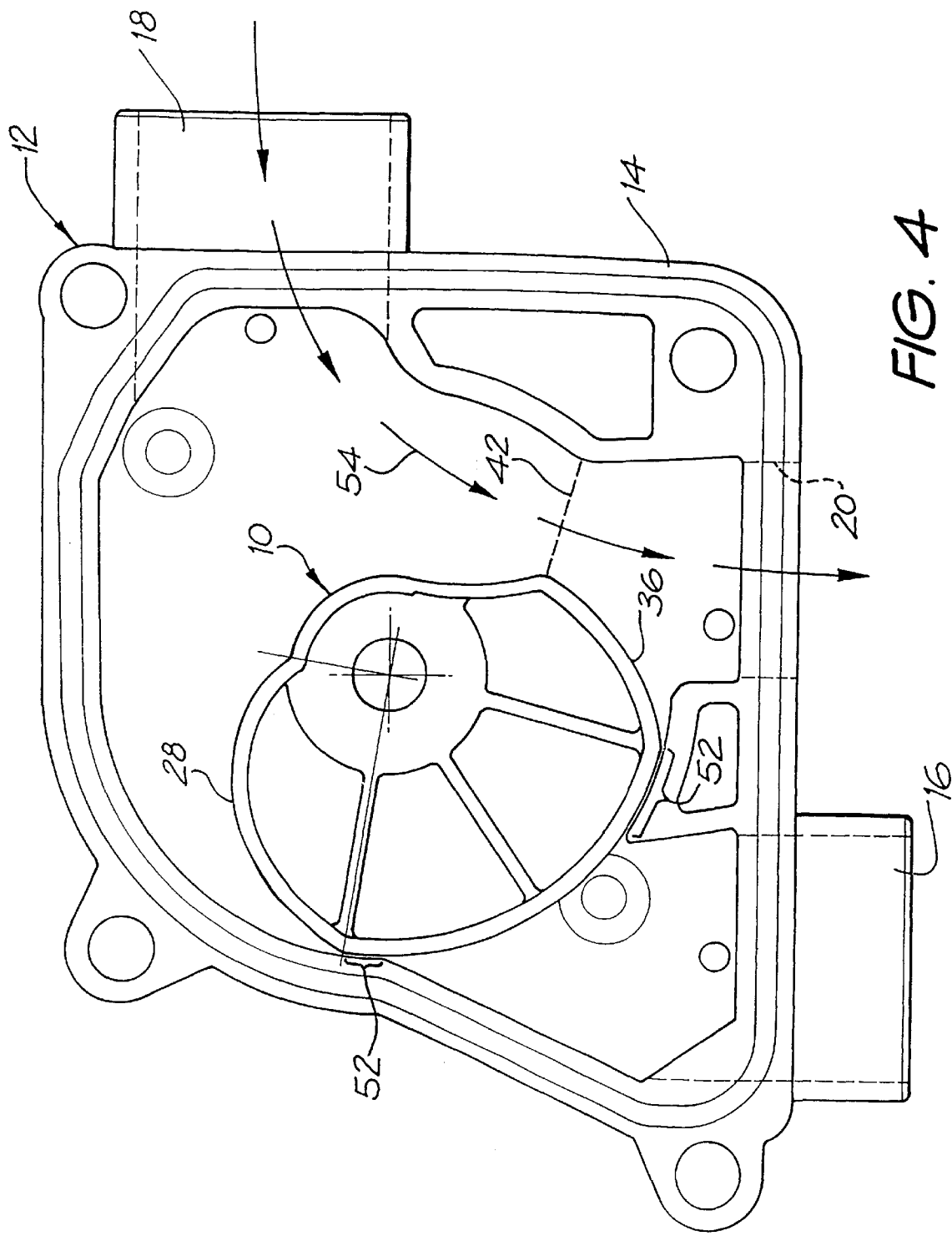
FIG. 4 is a top view of the valve shown in FIG. 1 with the inlet fully closed and the vent fully opened.

FIG. 4 shows the control member 10 placed in a position suitable for patient exhalation in which the control flow area 24 between the inlet 16 and outlet 18 is substantially closed whilst the flow area 42 between the outlet duct 18 and the vent 20 is maximised. This reduces the effort of patient exhalation because the patient is exhaling against a lower pressure. The exhaled gas travels in the direction indicated by arrows 54.

Similar to regions 46, the overlapping regions 52 improve sealing between the control member 10 and interior of the housing 14.

In the embodiment shown, the rate of change of the flow control area 42 adjacent the vent 20 is also substantially linear with respect to the angular movement of the control member 10 between the end positions 38 and 40.

Figure 6:
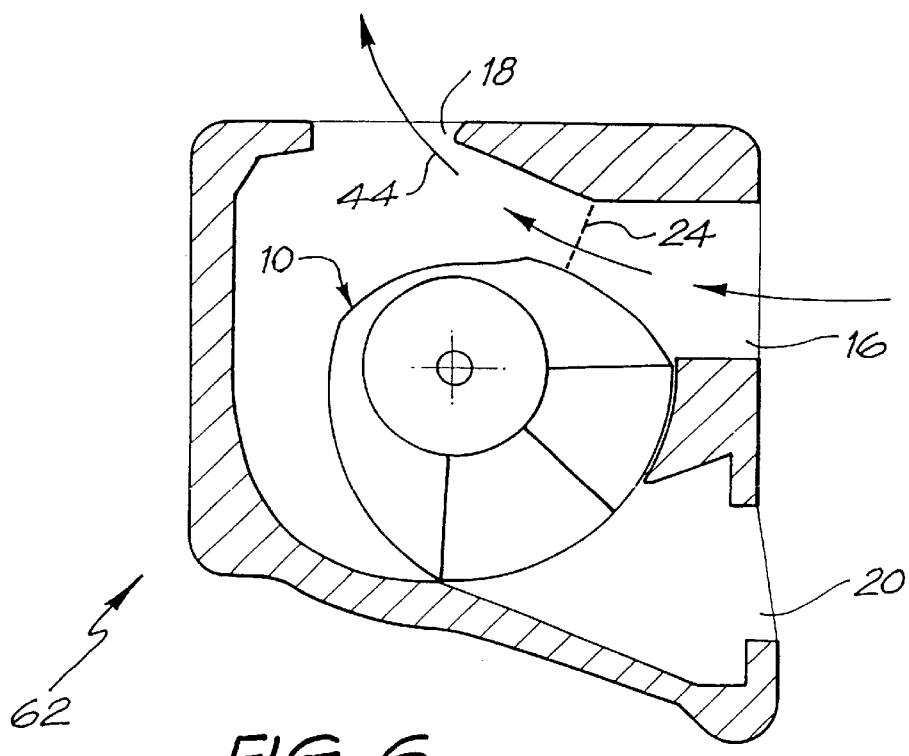
FIG. 6 is a schematic top view of another valve having the first embodiment of the flow control member with the cover removed and with the inlet partially restricted and the vent fully closed.
Figure 7:
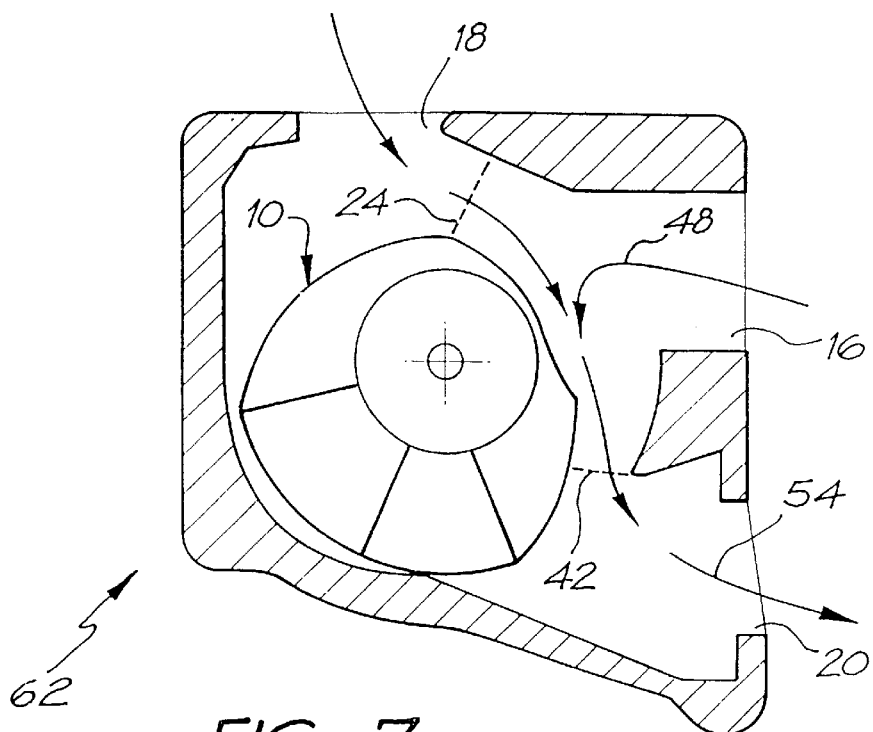
FIG. 7 is a schematic top view of the valve shown in FIG. 6 with the inlet partially restricted and the vent partially open.

FIGS. 6 and 7 show the control member 10 used in another flow diverting valve 62 that is also suitable for NIPPV. Like reference numerals to those used in describing the first embodiment will be used to denote like features. The positions of the inlet 16 and the vent 20 in the valve 62 are reversed relative to the valve 12. The flow of gas from the inlet 16 to the outlet 18 is never stopped in the valve 62, in contrast to the valve 12.

FIG. 6 shows the central member 10 placed in a position suitable for patient inhalation in which all of the supplied gas flows from the inlet 16 to the outlet 18, as indicated by the arrows 44. The control flow area of the vent 20 is closed in this position.

FIG. 7 shows the control member 10 placed in a position suitable for patient exhalation in which the control flow area 42 adjacent the vent 20 partially opened. This allows some of the supplied gas to flow to the vent 20 and reduces the effort of patient exhalation because the patient is exhaling against a lower pressure. The gas exhaled by the patient that exits to atmosphere through the vent 20, is indicated by the arrows 54.

When NIPPV is used to treat respiratory failure, it requires very fast changes in pressure and flow of gas delivered to the patient. Typically optimum NIPPV allows for less than a 100 ms time span for changing mask pressure at the transitions from inhalation to exhalation and from exhalation to inhalation throughout the respiratory cycle. It can also be desirable to effect changes in mask pressure within an inspiratory phase or an expiratory phase on a similar time scale. It is important for gas supply apparatus used in NIPPV to provide very fast pressure and flow transitions and be able to accurately adjust the particular mask pressure for the patient's requirements. The preferred form of the valves 12 and 62 respectively described with reference to FIGS. 1 to 4 and FIGS. 6 and 7 are suitable for meeting these requirements.

The preferred embodiment shows a direct linear relationship between the control member rotation and change in control flow area. It will be appreciated by those skilled in the art that minor adjustments to the shape of control member can be performed, particularly near the closed position, to overcome air friction surface effects and housing shape factors and maintain a substantially linear pressure/flow rate relationships relative to the control member position. The materials and surface texture of the control member and adjacent interior housing wall can also have an influence on any such non-linearities that arise near the closed position.

Another advantage of the valves 12 and 62 is that their gas flow paths are sealed with respect to any associated electronic components. This reduces the risk of fumes or smoke from failing electric components being supplied to the patient.

Whilst the invention has been described with reference to specific examples, it will be appreciated by those skilled in the art that the invention may be embodied in many other forms.

We claim:

1. A control member for a valve, the valve having an inlet, and outlet and a primary flow path therebetween, the control member being rotatable to alter a control flow area of the primary flow path, the control flow area being of a rectangular shape having a side defined by a wall of a valve interior, a side defined by a wall of a control member exterior, a bottom defined by a floor of the valve interior and a top defined by a roof of the valve interior wherein the control member exterior is so configured that rotation of the control member alters a distance between the control member exterior and the wall of the valve interior to alter the control flow area of the primary flow path, with the amount of rotation of the control member between two predetermined end positions and the alteration in the control flow area of the primary flow path being substantially linearly proportional.

2. The control member as claimed in claim 1, wherein at all rotational positions of the control member, the control flow area is the minimum cross-sectional area between the valve interior and the control member exterior downstream of the inlet.

3. The control member as claimed in claim 1, wherein the rotation of the control member is controlled by at least one of a stepper motor, servo motor and other rotary actuator.

4. The control member as claimed in claim 1, wherein the two predetermined end positions correspond to the control flow area being at a maximum and a minimum respectively.

5. The control member as claimed in claim 4, wherein the minimum control flow area is the primary flow path being substantially occluded or closed.

6. The control member as claimed in claim 1, wherein the valve includes a vent to atmosphere and a secondary flow path between the valve outlet and the vent, wherein the rotation of the control member is also adapted to alter a control flow area of the secondary flow path.

7. The control member as claimed in claim 6, wherein at all rotational positions of the control member the control flow area of the secondary flow path is the minimum cross-sectional area between the housing interior and the control member exterior upstream of the vent.

8. The control member as claimed in claim 6, wherein the control member is adapted such that increasing the control area of the primary flow path simultaneously decreases the control area of the secondary flow path and vice versa.

9. The control member as claimed in claim 6, wherein when the control flow area of the primary flow path is maximised or fully opened the control flow area of the secondary flow path is minimised or fully closed, and when the control flow area of the primary flow path is minimised or fully closed the control flow area of the secondary path is at least partially opened.

10. The control member as claimed in claim 6, wherein when the control flow area of the primary flow path is maximised or fully opened the control flow area of the secondary flow path is minimised or fully closed, and when the control flow area of the primary flow path is minimised or fully closed the control flow area of the secondary path is fully opened.

\* \* \* \* \*

UNITED STATES PATENT AND TRADEMARK OFFICE
CERTIFICATE OF CORRECTION

PATENT NO.   : 6,269,839 B1
DATED        : August 7, 2001
INVENTOR(S)  : Wickham et al.

It is certified that error appears in the above-identified patent and that said Letters Patent is hereby corrected as shown below:

<u>Title page,</u>
Change item [22] to read as follows: -- [22] Filed August 6, 1999 --

Signed and Sealed this

Twenty-third Day of October, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,269,839 B1
DATED : August 7, 2001
INVENTOR(S) : Wickham et al.

It is certified that error appears in the above-identified patent and that said Letters Patent is hereby corrected as shown below:

<u>Title page,</u>
Item [73], Assignee, delete "Assignee:  ResMed (R&D) Limited (AU)" and insert therefor -- [73] Assignee:  ResMed Limited (AU) --

Signed and Sealed this

Twenty-fifth Day of May, 2004

JON W. DUDAS
*Acting Director of the United States Patent and Trademark Office*